(12) United States Patent
Collins et al.

(10) Patent No.: US 7,641,656 B2
(45) Date of Patent: Jan. 5, 2010

(54) PROSTHETIC CUP

(75) Inventors: Simon Collins, Gloucester (GB); Ian Emslie, Cirencester (GB)

(73) Assignee: Corin Limited, Gloucestershire (GB)

( * ) Notice: Subject to any disclaimer, the term of this patent is extended or adjusted under 35 U.S.C. 154(b) by 981 days.

(21) Appl. No.: 10/942,394

(22) Filed: Sep. 16, 2004

(65) Prior Publication Data

US 2005/0085820 A1    Apr. 21, 2005

(30) Foreign Application Priority Data

Sep. 17, 2003    (GB) ................ 0321801.3

(51) Int. Cl.
*A61B 17/00* (2006.01)

(52) U.S. Cl. .................... 606/79; 606/86 R (58) Field of Classification Search ... 623/22.21–22.39; 606/86, 96, 104, 79, 86 R, 86 A, 86 B, 291, 606/300–308, 325; 411/411–413, 424, 426
See application file for complete search history.

(56) References Cited

U.S. PATENT DOCUMENTS

| 4,611,587 | A | 9/1986 | Powlan |
| 4,623,351 | A | 11/1986 | Church |
| 5,180,382 | A | 1/1993 | Frigg et al. |
| 5,624,464 | A | 4/1997 | Wagner et al. |
| 5,769,856 | A * | 6/1998 | Dong et al. .................... 606/96 |
| 5,836,950 | A | 11/1998 | Hansson |
| 6,355,043 | B1 | 3/2002 | Adam |
| 6,620,200 | B1 | 9/2003 | Descamps et al. |
| 6,623,486 | B1 * | 9/2003 | Weaver et al. ................. 606/69 |
| 2002/0128657 | A1 | 9/2002 | Hansson |
| 2003/0045938 | A1 | 3/2003 | Kohrs et al. |
| 2003/0158556 | A1 | 8/2003 | Taras et al. |

FOREIGN PATENT DOCUMENTS

| EP | 1 029 519 A2 | 8/2000 |
| FR | 2 634 372 | 1/1990 |
| FR | 2 758 255 | 7/1998 |
| FR | 2 786 390 | 6/2000 |
| FR | 2 793 137 | 11/2000 |
| FR | 2 798 841 | 3/2001 |

(Continued)

*Primary Examiner*—Thomas C Barrett
*Assistant Examiner*—Michael J Araj
(74) *Attorney, Agent, or Firm*—Leydig, Voit & Mayer, Ltd.

(57) ABSTRACT

A bone tapping kit for cutting an internal thread into bone defining a bore. The kit comprises 1) a guide component with a threaded aperture which, when in position, is aligned with the bore, and 2) a tap having a first portion with a first diameter and an external thread designed to engage with the threaded aperture of the guide component, and a second portion having a second diameter which is smaller than the first diameter and a helical cutting edge designed so that it can be received into the bore and cut an internal thread therein. The guide component and tap are dimensioned so that when the tap is introduced into the guide component the first portion engages with the threaded aperture in the guide component before the helical cutting edge of the second portion engages with the bore. Thus, the thread configuration that is cut into the bore forms a continuation of the same helix defined by the internal thread of the aperture of the guide member.

15 Claims, 6 Drawing Sheets

FOREIGN PATENT DOCUMENTS

| | | |
|---|---|---|
| FR | 2 819 172 | 7/2002 |
| GB | 504 095 | 4/1939 |
| GB | 1 575 194 | 9/1980 |
| GB | 2 177 325 A | 1/1987 |
| JP | 10277052 A | 10/1998 |
| WO | WO 90/02526 | 3/1990 |
| WO | WO 95/11632 | 5/1995 |
| WO | WO 99/22672 | 5/1999 |

\* cited by examiner

PROSTHETIC CUP

FIELD OF THE INVENTION

The present invention relates to a bone tapping kit and a method of using the same.

"Dysplasia" means "improper development or formation" and dyplasia of the hip refers to a group of disorders of the hip in which the acetabulum and femoral head do not interact in a normal fashion. In particular, the femoral head is not contained within the acetabulum and is free to slide, generally in a superior direction.

Figure 1:
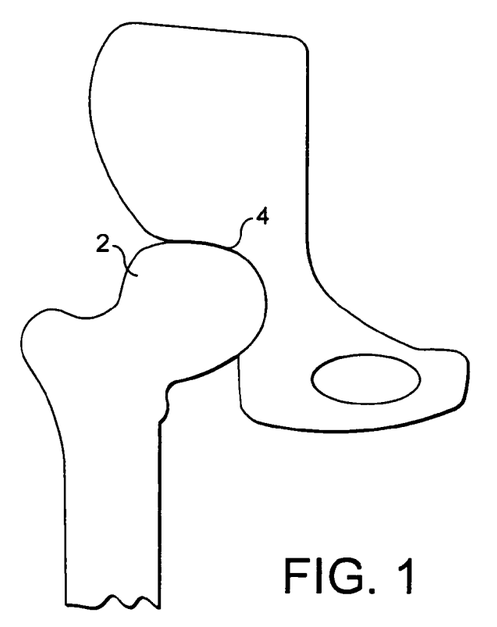
FIG. 1 shows a diagrammatic representation of a "normal" hip.

In a normal hip, as shown in FIG. 1, the femoral head 2 is contained within the acetabulum 4 and the contacting surfaces are congruous and concentric.

Figure 2:
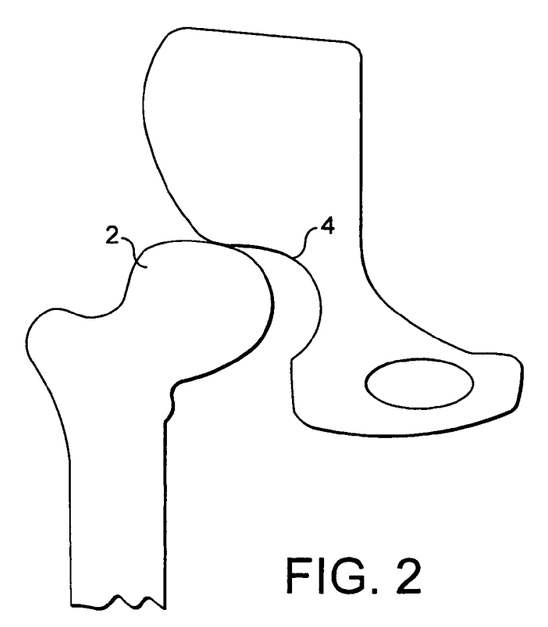
FIG. 2 shows a diagrammatic representation of a "dysplastic" hip.

In a dysplastic hip the femoral head and the acetabular cup are not congruent and the femoral head moves within the acetabulum in a non-concentric manner. FIG. 2 shows a dysplastic hip and, as can be seen, the acetabulum 4 is shallower than in the normal hip shown in FIG. 1 and the superior side of the acetabulum, in particular, is significantly shallower and no longer contains the femoral head 2 in position within the acetabulum 4. In very severe cases the femoral head may become dislocated.

Dysplasia of the hip is a common cause of osteo-arthritis in the young which, in terms of hip surgery, are defined as patients between 20-60 years. Hip surgery, for example in a Total Hip Replacement procedure or Hip Resurfacing procedure, often requires the insertion into the acetabulum of an acetabular cup to retain either a prosthetic or resurfaced femoral head. However, in the case of patients with dysplasia of the hip this can be particularly difficult since the acetabulum in a dysplastic hip is significantly shallower than in a normal hip. This means that the surface available for fixation of the acetabular cup may not be sufficient to provide adequate fixation.

A similar problem may also arise in those cases where it is necessary to replace an acetabular cup in a subsequent (revision) procedure. In particular, the act of preparing the acetabulum to receive the first acetabular cup may have left insufficient bone to provide adequate fixation for the second. It is therefore desirable to provide an acetabular cup with enhanced fixation for use in hip surgery.

A number of solutions have previously been suggested for overcoming problems with fixation of the acetabular cup, including those due to dysplasia of the hip.

One suggested solution is to fill any superior defect using either a bone graft or bone cement. However, cement may crack and fail, or not provide sufficient fixation in an active patient. Likewise, the use of bone grafts is not desirable since this requires further surgery to remove such a graft from another area of the patients' body. Furthermore, it may take longer than desired for the graft to integrate. As is well known, it is advantageous to mobilize a patient as soon as possible after a hip replacement operation to minimize bone density loss and maximize the likelihood of a successful procedure.

Another suggestion has been to adapt an acetabular cup for use in a dysplastic hip by providing a lug on a superior side of the cup which extends coplanar with a rim of the cup. The lug is provided with a threaded aperture and a hole is drilled into the underlying bone so as to be in alignment with the aperture. A screw is passed through the aperture where it threadingly engages with the lug and into the bone. However, this method of fixation raises a number of problems. Firstly, as the screw engages the bone it creates a reaction force which acts to push the acetabular cup out of the acetabulum. If the reaction force produced by the screw is not sufficiently countered then it may compromise the primary fixation of the cup which is often achieved by a press-fit of a generally hemispherical form into the acetabulum. Secondly, because of the disposition of the lug, a significant portion of the length of the screw between the lug and the bone surface is unutilized. And thirdly, because no stop is provided when the screw is fully home there is a risk of the screw being over tightened with the result that the acetabular cup may be again unseated from the acetabulum.

BRIEF SUMMARY OF THE INVENTION

According to a first aspect of the present invention there is provided a bone tapping kit for cutting an internal thread in bone defining a bore, the kit comprising: a guide component adapted to overlie the bone and having a threaded aperture in alignment with the bore; and a tap comprising a first portion having a first diameter and a second portion having a second diameter, the second diameter being smaller than the first diameter, the first portion having an external thread adapted to threadingly engage the threaded aperture of the guide component and the second portion having a helical cutting edge adapted to be received within the bore and cut the internal thread, the guide component and tap being relatively dimensioned such that upon introduction of the tap into the threaded aperture with the second portion towards the bone, the first portion of the tap threadingly engages the threaded aperture before the helical cutting edge engages the bone.

Advantageously, the threaded aperture defines an axis and has an axial dimension which is greater than the axial length of the second portion of the tap.

Advantageously, the first portion and second portion are contiguous and meet at a shoulder.

Alternatively, the first and second portions are interconnected by an intermediate portion, the intermediate portion tapering from the first diameter adjacent the first portion to the second diameter adjacent the second portion.

Advantageously, the helical cutting edge provided on the second portion of the tap has the same pitch as the external thread provided on the first portion of the tap and the same angular displacement as a continuation of the helix defined by said external thread.

Preferably, the helical cutting edge provided on the second portion of the tap is adapted to cut an internal thread capable of threaded engagement with a corti/cancellous bone thread.

Advantageously, the guide component comprises a prosthetic device to be secured to the bone by means of a fixation member passing through the threaded aperture.

Preferably, the prosthetic device comprises a cup for use in a ball and socket joint, the cup comprising an outer surface, an inner articulating surface, and a flange extending outwardly from the cup and away from the inner articulating surface, the threaded aperture being provided in said flange.

Advantageously, the kit previously described when having the guide component as a prosthetic device may find use in combination with a fixation member as previously described.

Preferably, the first thread configuration of the fixation member and the external thread provided on the first portion of the tap are both adapted to threadingly engage the threaded aperture of the guide component.

Preferably, the second thread configuration of the fixation member is adapted to threadingly engage the internal thread cut by the helical cutting edge provided on the second portion of the tap.

Advantageously, upon removal of the tap from the guide component and introduction of the fixation member into the threaded aperture, the second thread configuration of the fixation member threadingly engages the internal thread cut by the helical cutting edge provided on the second portion of the tap before the first thread configuration of the fixation member threadingly engages the threaded aperture of the guide component.

According to a second aspect of the present invention there is provided a method of cutting an internal thread in a bone defining a bore comprising the steps of: providing a guide component having a threaded aperture; aligning the threaded aperture with the bore; providing a tap comprising a first portion having a first diameter and a second portion having a second diameter, the second diameter being smaller than the first diameter, the first portion having an external thread adapted to threadingly engage the threaded aperture of the guide component and the second portion having a helical cutting edge adapted to be received within the bore, the helical cutting edge having the same pitch as the external thread provided on the first portion and the same angular displacement as a continuation of the helix defined by the external thread; introducing the tap into the threaded aperture of the guide component with the second portion directed towards the bone; threadingly engaging the first portion of the tap with the threaded aperture before engaging the helical cutting edge with the bone; and rotating the tap while maintaining said threaded engagement.

According to a third aspect of the present invention there is also provided a method of securing a prosthesis with respect to a bone defining a bore, the method comprising the steps of: providing a prosthesis defining a threaded aperture; providing a fixation member comprising a first portion having a first diameter and a first thread configuration and a second portion having a second diameter and a second thread configuration, the second diameter being smaller than the first diameter, the first thread configuration being adapted to threadingly engage the threaded aperture of the prosthesis and the second thread configuration having the same pitch as the first thread configuration and the same angular displacement as a continuation of the helix defined by the first thread configuration; cutting an internal thread in the bore according to the method previously described using the prosthesis as the guide component; removing the tap; introducing the fixation member through the threaded aperture with the second portion directed towards the bone; and threadingly engaging the second thread configuration with the internal thread before engaging the first thread configuration with the threaded aperture.

According to one arrangement there is provided, a prosthetic cup for use in a ball and socket joint, the cup comprising an outer surface, an inner articulating surface, a rim extending between the outer surface and the inner articulating surface and a flange extending outwardly from the cup and away from the inner articulating surface, at least a portion of the flange being inclined with respect to a plane defined by the rim and having an aperture adapted to receive a fixation member.

Advantageously, the flange comprises a first portion which extends outwardly from the cup and is substantially co-planar with the rim and a second portion which extends from the first portion at an end remote from the cup, the second portion being inclined with respect to the first portion.

Preferably, the inclined portion is inclined at an angle of up to 50° to a plane defined by the rim.

More preferably, the inclined portion is inclined at an angle of between 5° and 25° to a plane defined by the rim.

Most preferably, the inclined portion is inclined at an angle of between 10° and 20° to a plane defined by the rim.

Advantageously, the inclined portion comprises a plurality of apertures adapted to receive a fixation member.

Advantageously, the or each aperture is threaded.

Advantageously, the or each aperture is countersunk.

Advantageously, the outer surface is provided with one or more splines.

Advantageously, the prosthetic cup also comprises a supero-medial peg.

Advantageously, the rim of the prosthetic cup is provided with one or more recesses adapted to receive a corresponding number of projections of an introducing tool.

Advantageously, the outer surface of the prosthetic cup is substantially hemi-spherical save that an equatorial diameter in a plane parallel to that defined by the rim is slightly greater than a polar diameter in a plane at right angles thereto.

Advantageously, the outer surface and an under surface of the flange are provided with a coating to promote enhanced osteo-integration.

Advantageously, the prosthetic cup is an acetabular cup.

According to a further arrangement there is provided a bone/prosthesis fixation member comprising a first portion having a first diameter and a first thread configuration and a second portion having a second diameter and a second thread configuration, the second diameter being smaller than the first diameter and the second thread configuration having the same pitch as the first thread configuration and the same angular displacement as a continuation of the helix defined by the first thread configuration.

Advantageously, the cross-sectional profile of the second thread configuration is the same as that of the first thread configuration.

Preferably, the cross-sectional profile of the second thread configuration is different from that of the first thread configuration.

Advantageously, the second thread configuration is a corti/cancellous bone thread.

Advantageously, the first and second portions are interconnected by an intermediate portion, the intermediate portion tapering from the first diameter adjacent the first portion to the second diameter adjacent the second potion.

Preferably, the intermediate portion is threaded, the thread of the intermediate portion being contiguous with both the first and second thread configurations.

Alternatively, the intermediate portion is unthreaded such that the first and second thread configuration are axially spaced.

Alternatively, the first and second portions are contiguous and meet at a shoulder.

Advantageously, the fixation member further comprises a head adjacent the first portion, the head being provided with a formation with which to engage a complimentary formation of a tool adapted to rotate the head about a longitudinal axis of the fixation member.

Preferably, the head is of frustroconical shape and tapers towards the first portion.

Advantageously, the fixation member further comprises a self tapping tip adjacent the second portion.

Advantageously, a fixation member as previously described may find use in combination with a prosthetic cup as previously described.

Advantageously, the prosthetic cup is adapted to threadingly engage the first thread configuration of a respective fixation member.

Advantageously, the or each aperture of the prosthetic cup is defined, at least in part, by a formation adapted to engage a complementary formation provided on the fixation member, the respective formations interengaging when the fixation member is received within the aperture to inhibit rotation of the fixation member with respect to the cup.

Advantageously, the or each aperture of the prosthetic cup is defined, at least in part, by a beveled surface and the fixation member is provided with a head shaped to engage the beveled surface when the fixation member is received within the aperture.

According to another arrangement there is provided a tool for use in introducing a prosthetic cup into a body, the tool comprising a stem, a head plate attached to the stem, means for selectively retaining the prosthetic cup with respect to the tool and a flange extending outwardly from the head plate and away from the stem, at least a portion of the flange being inclined with respect to a plane defined by the head plate.

Advantageously, the flange comprises a first portion which extends outwardly from the head plate and is substantially co-planar therewith and a second portion which extends from the first portion at an end remote from the head plate, the second portion being inclined with respect to the first portion.

Advantageously, the inclined portion is inclined at an angle of up to 50° to a plane defined by the head plate.

Preferably, the inclined portion is inclined at an angle of between 5° and 25° to a plane defined by the head plate.

More preferably, the inclined portion is inclined at an angle of between 10° and 20° to a plane defined by the head plate.

Advantageously, a tool as previously described may find use in combination with a prosthetic cup as previously described.

Advantageously, the prosthetic cup is provided with one or more formations with which to engage a one or more complimentary formations provided on the tool, the formations being selectively engageable to retain the cup with respect to the tool.

Advantageously, the inclined portion of the tool is provided with one or more apertures, the or each aperture provided in the inclined portion of the tool being in alignment with a respective aperture provided in the inclined portion of the prosthetic cup when the prosthetic cup is mounted to the tool.

Preferably, the or each aperture provided in the inclined portion of the tool is adapted to receive an end of a guide tube.

Advantageously, the combination of the tool and prosthetic cup previously described may find use in combination with a fixation member, as previously described, wherein the or each aperture provided in the inclined portion of the tool has an internal diameter larger than the first diameter of the fixation member.

BRIEF DESCRIPTION OF THE DRAWINGS

Preferred embodiments of the invention will now be described, by way of example, with reference to the accompanying drawings, in which.

DETAILED DESCRIPTION OF THE INVENTION

Figure 3:
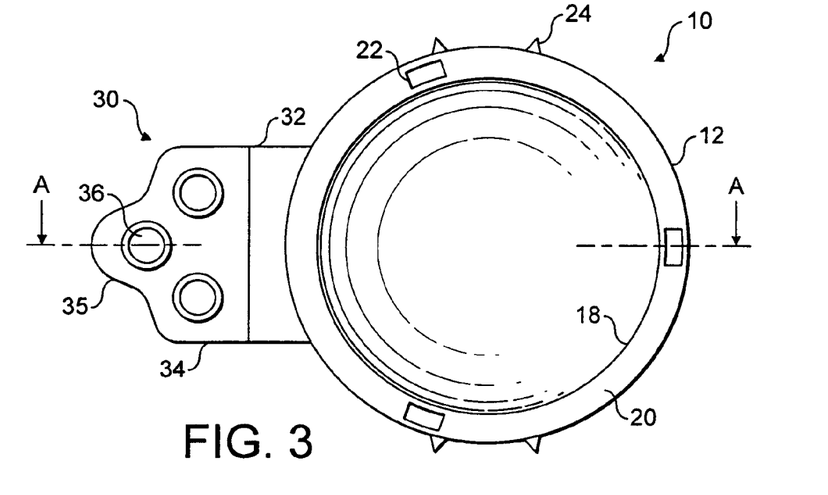
FIG. 3 shows a plan view of an acetabular cup.
Figure 4:
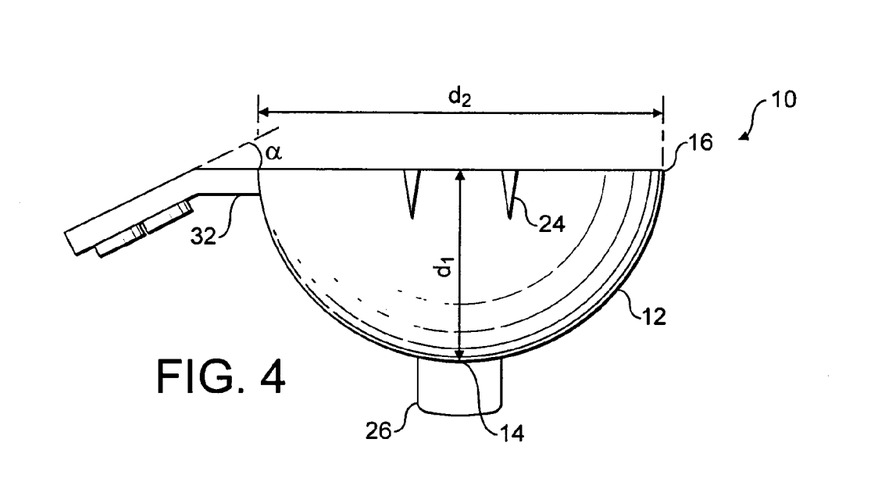
FIG. 4 shows a side view of the acetabular cup of FIG. 3.
Figure 5:
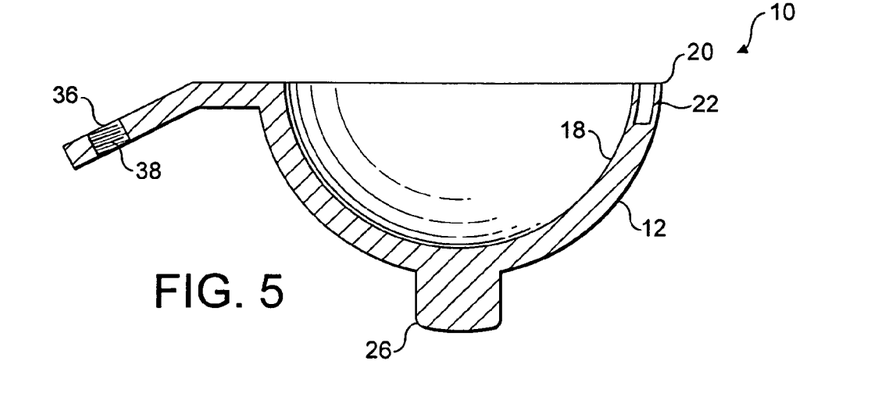
FIG. 5 shows a section A-A through the acetabular cup of FIG. 3.

Referring to FIGS. 3 to 5 there is shown an acetabular cup 10 which has a part-circular outer surface 12 which is of an appropriate diameter to fit into the acetabulum of a patient. The acetabular cup 10 has an outer equatorial edge 16 and defines a pole 14. Although FIGS. 4 and 5 show the outer surface 12 as having a perfect hemi-spherical shape, advantageously the outer surface 12 may be equatorially expanded. In other words, while the diameter $d_1$ at the pole 14 corresponds to the diameter of the prepared acetabulum, the diameter $d_2$ at the outer equatorial edge 16 may be somewhat greater by perhaps 1 to 3 mm. An equatorially expanded outer surface 12 provides the advantage that a press-fit is provided between the acetabular cup 10 and the acetabulum at the mouth of the device and a line-to-line fit at the pole 14. This results in an improved stress distribution to the patient's acetabulum.

The acetabular cup 10 also has a part circular, typically hemi-spherical or substantially hemi-spherical, articulating surface 18 having a diameter suitable for receiving a prosthetic or resurfaced femoral head, not shown. The acetabular cup 10 is preferably formed of metal, preferably a high carbon cobalt chrome-alloy, although it could be formed of a ceramic material such as zirconia or alumina. Whatever the material, the surface may be modified. It will also be understood that the acetabular cup 10 may be provided with a UHMWPE (Ultra High Molecular Weight Polyethylene) liner if desired, which will then provide the articulating surface in place of the acetabular cup itself.

An annular rim 20 extends between the outer surface 12 and the articulating surface 18. The rim 20 is substantially planar and is provided with three angularly spaced recesses 22 to facilitate introduction of the acetabular cup 10 into the acetabulum. The recesses 22 open out only into the rim 20 and are spaced from both the outer surface 12 and the articulating surface 18.

To improve the fixation of the acetabular cup 10 to the acetabulum the outer surface 12 may be textured and/or comprise a plurality of splines 24. The splines 24 inhibit rotation of the cup 10 with respect to the acetabulum. Preferably, two sets of splines 24 are provided on opposing sides of the acetabular cup 10 at locations spaced from the recesses 22.

Optionally, the acetabular cup 10 may further comprise a supero-medial peg 26 which extends radially outwardly from the pole 14 of the outer surface 12 to provide enhanced initial fixation.

The acetabular cup 10 further comprises a flange 30. The flange 30 comprises a first portion 32 which extends radially outwardly from the outer surface 12 and has an upper surface 33 substantially co-planar with the rim 20. The flange 30 also comprises a second portion 34 which is inclined with respect to the first portion 32 and extends from an end of the first portion 32 remote from the outer surface 12 in a radially outwardly and downwardly direction with respect to the rim 20. The second portion 34 is inclined with respect to the first portion 32 at an angle α of up to approximately 50°. Preferably the angle of inclination (α) lies within the range 5°-25° while more preferably still the angle of inclination (α) lies within the range 10°-20°. Most preferably of all the angle of inclination (α) is approximately 15°. The second portion 34 of the flange 30 is sized so as to accommodate a number of countersunk threaded apertures 36 through which fixation members may be received. Although three apertures 36 are shown in FIG. 3, it will be understood that the use of two fixation members may be sufficient to adequately secure the acetabular cup 10 within the acetabulum. In some cases only one fixation may be required.

The outer surface 12 of the acetabular cup 10 and the under surface of the flange 30 may be coated with an artificial bone substitute material such as hydroxyapatite (HAP) to provide optimum long term osteo-integration. Alternatively, the outer surface 12 may have a porous coated or plasma coated surface to enhance fixation of the acetabular cup 10 within the acetabulum. One particularly preferred coating option is a dual coating comprising a plasma sprayed layer of either Cobalt Chromium or Titanium, followed by a layer of hydroxyapatite. The use of such dual coatings combines the enhanced osteo-integration provided by hydroxyapatite and the increased surface area provided by the Cobalt Chromium or Titanium.

Figure 6:
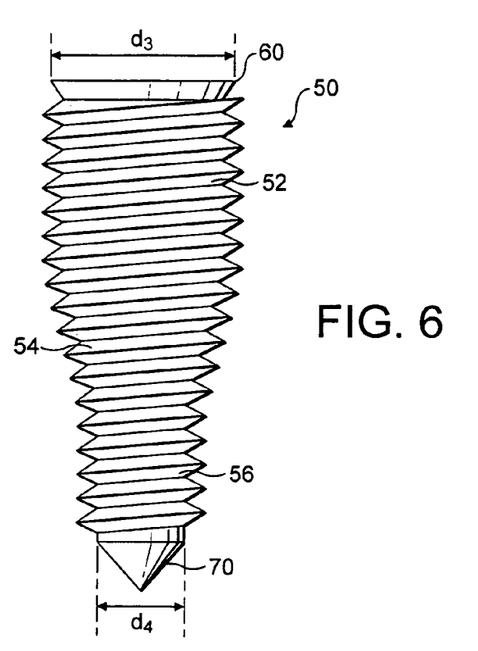
FIG. 6 shows a cross-sectional view of a fixation device.

A fixation member 50 is shown in FIG. 6. The fixation member 50 comprises an upper portion 52, a lower portion 56 and a central portion 54 interconnecting the upper and lower portions 52 and 56. The upper portion 52 has a diameter $d_3$ and the lower portion 56 a diameter $d_4$, where $d_3$ is greater than d4. The fixation member 50 is provided with a thread 58, which is shown as being continuous and of constant pitch over the upper, central and lower portions, 52, 54 and 56. However, it will be understood that the thread may be omitted from the central portion 54 and that the same or different thread configurations may be provided on the upper and lower portions 52 and 56 provided that the thread configurations on both portions have the same pitch and provided that the thread configuration on the lower portion 56 starts at a location so as to be a continuation of the same helix defined by the thread configuration on the upper portion 52 albeit of reduced radius.

What may be different however, is the cross-sectional shape of the two thread configurations. Thus the thread configuration on the upper portion 52 may comprise a metric thread, for example a metric 8 mm, M8, thread while the thread configuration on the lower portion 56 may be of a corti/cancellous bone thread design. Nonetheless, if desired, the thread configuration on the upper and lower portions 52 and 56 may be of the same cross-sectional shape. The thread configuration on the lower portion 56 is preferably of a corti/cancellous bone thread design in order to provide secure attachment to the bone surrounding the acetabulum and the thread configuration on the upper portion 52 may also be of this design. The thread configuration on the upper portion 52 is required to threadingly engage the threaded apertures 36 provided in the flange 30. Thus these threaded apertures 36 may be provided with a mating corti/cancellous bone thread design. Alternatively, the threaded apertures 36 may be provided with a metric thread such as a metric 8 mm, M8, thread since a corti/cancellous bone thread will nonetheless threadingly engage a mating metric thread of the same diameter provided that the threads are engineered correctly.

The fixation member 50 further comprises a frustoconical head 60 having a standard hexagonal drive with which to receive a hexagonal insertion tool. However, it will be apparent that other drive mechanisms may be suitable.

The fixation member 50 further comprises a tip 70 which is conical in shape and may be fluted to allow self tapping.

The fixation member 50 may have a length in the range from 10 to 70 mm. Preferably the fixation member may have a length in the range from 20 to 50 mm.

Figure 7:
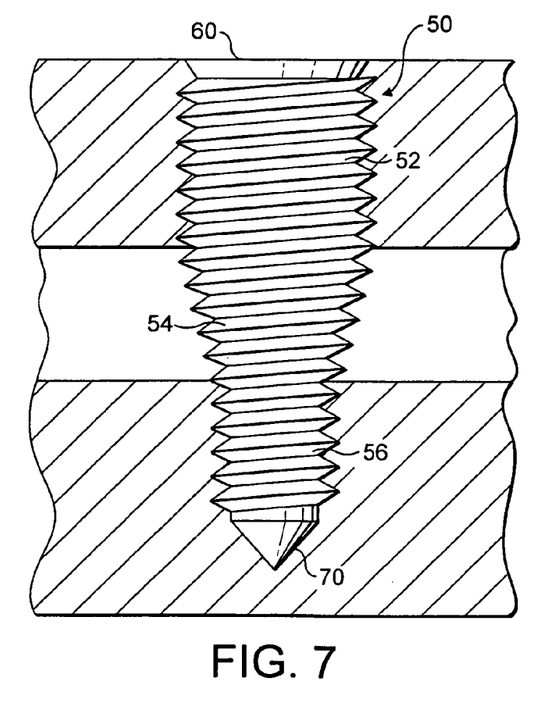
FIG. 7 shows the fixation device of FIG. 6 when in use.

FIG. 7 shows the fixation member 50 when positioned in use, with the thread configuration omitted for clarity. The upper portion 52 is engaged in one of the threaded apertures 36 to a depth such that the head of the fixation member 60 is flush with an upper surface of the flange 30. At the same time the frustoconical side wall of the head 60 engages a correspondingly shaped bevel surrounding the aperture 36 to lock the head 60 into the flange 30 to prevent the fixation member from loosening. In contrast, the lower portion 56 is engaged in the acetabulum while the central portion 54 lies between the flange 30 and the acetabulum.

Although the central portion 54 has been described as tapering from the diameter of the upper portion 52 to the diameter of the lower portion 56, in an alternative embodiment the central portion may be omitted such that the upper portion 52 is contiguous with the lower portion 56 and the upper and lower portions meet at a step change in the diameter of the fixation member 50.

Figure 8:
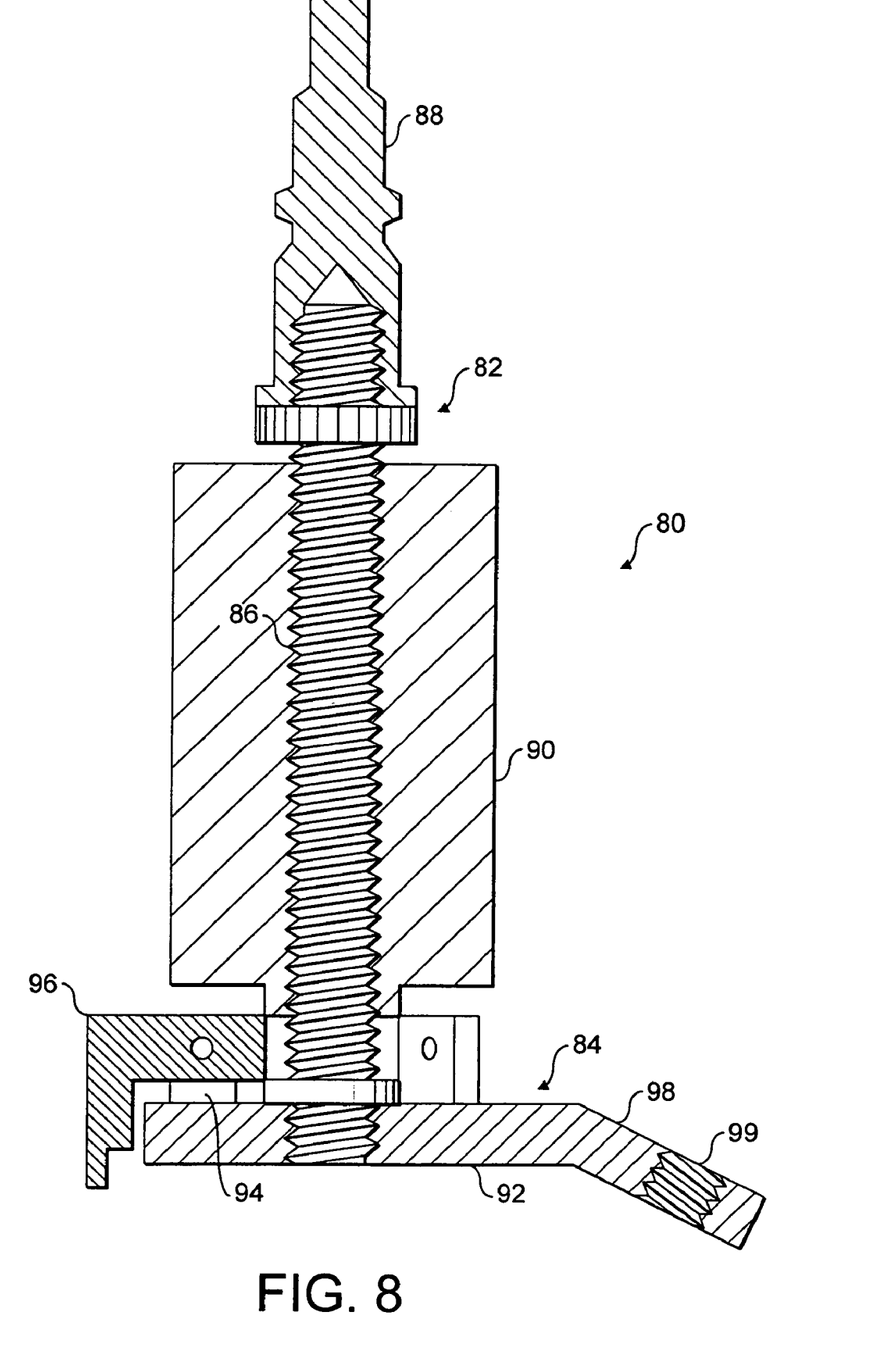
FIG. 8 shows a longitudinal, cross-sectional view of an introducing tool.

Referring now to FIG. 8 of the drawings, an introducing tool 80 is shown. The introducing tool 80 comprises an elongate stem 82 and a head 84. The stem 82 comprises an externally threaded part 86 and a handle 88 pivotally connected to the threaded part 86. An internally threaded sleeve 90 is mounted on the threaded part 86 of the stem 82 for a purpose which will become apparent.

The head 84 comprises a plate 92 having three upstanding lugs 94. A generally L-shaped finger 96 is pivotally mounted on each of the lugs 94. The free ends of the fingers 96 are moveable radially inwards towards an elongate axis of the stem 82 and into a position in which they are insertable into the recesses 22 in the rim 20 of the acetabular cup 10. Once the fingers 96 have been inserted in the recesses 22, the threaded sleeve 90 can be rotated to bring one end of the sleeve into contact with the fingers 96. This causes the free ends of the finger 96 to pivot radially outwards and to be urged into frictional engagement with the walls of the recesses 22. The surgeon may then use the introducing tool 80 to manipulate the acetabular cup 10. In order to disengage the acetabular cup 10, the surgeon simply rotates the sleeve 90 in the opposite direction to release the fingers 96 from frictional engagement with the recesses 22. The introducing tool 80 may then be removed from the acetabular cup 10.

By providing the recesses 22 in the rim 20 of the acetabular cup 10, the articulating surface 18 of the acetabular cup is not compromised and this helps to minimize the wear between the femoral head and the interior surface of the cup.

Figure 9:
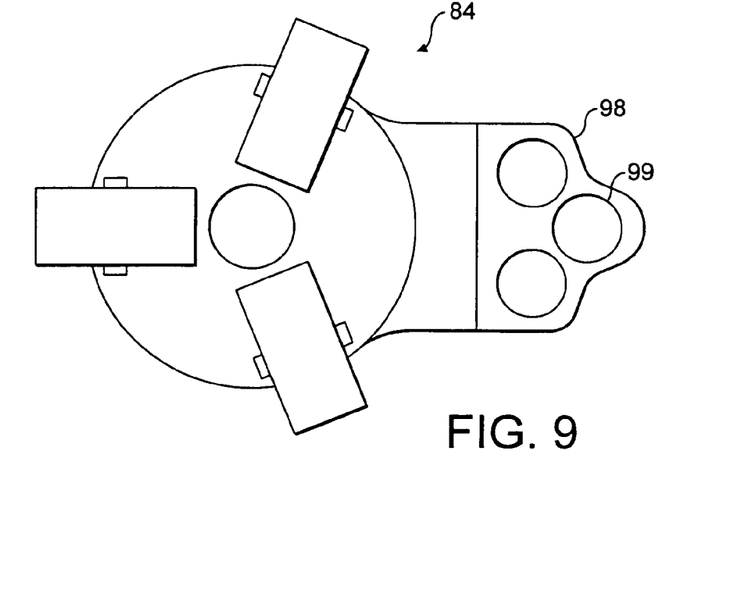
FIG. 9 shows a plan view of a head of the introducing tool of FIG. 8.

In addition to the upstanding lugs 94, the plate 92 further comprises a flange plate 98 configured to correspond with the flange 30 of the acetabular cup 10. Looking at FIG. 8 it can be seen that the flange plate 98 is inclined to the plate 92 by the same angle and in the same direction as the second portion 34 of the flange 30 is inclined to the first portion 32. Furthermore, looking at FIG. 9 it can be seen that the flange plate 98 is provided with three guide apertures 99 which are disposed so as to be concentrically aligned with the apertures 36 provided in the flange 30 of the acetabular cup 10 once the acetabular cup is mounted on the introducing tool 80. The diameter of the guide apertures 99 is however somewhat larger than that of the apertures 36.

Figure 10:
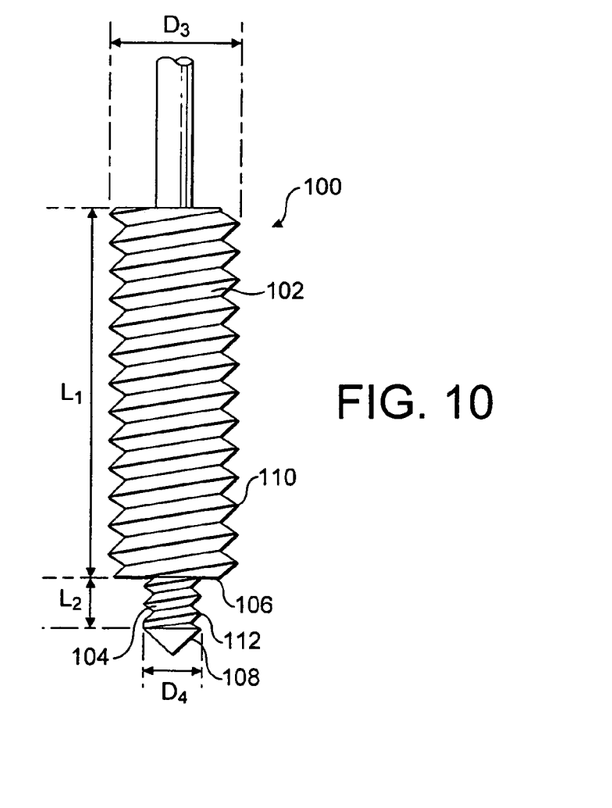
FIG. 10 shows a cross-sectional view of a starter tap according to the present invention.

FIG. 10 shows a starter tap 100 comprising an upper portion 102, a lower portion 104 and a tip 108. The upper portion 102 has the same diameter $d_3$ as the upper portion 52 of the fixation member 50 and the lower portion 104 has the same diameter $d_4$ as the lower portion 56. The upper and lower portions 102 and 104 meet at a radially projecting shoulder 106. A helical thread 110 is provided on the exterior of the upper portion 102 which is capable of threaded engagement with the apertures 36 provided in flange 30. By contrast, the exterior of the lower portion 104 is provided with a helical cutting edge 112 having the same pitch as thread 110 with which to form an internal thread capable of threaded engagement with the helical thread provided on the lower portion 56 of the fixation member 50. The length $L_1$ of the upper portion 102 is significantly longer than the length $L_2$ of the lower portion 106. The upper portion 102 is adapted to be connected to a handle or similar tool, not shown, in order to facilitate the manipulation of the starter tap 100 and in particular to rotate the starter tap about a longitudinal axis.

A method of introducing the acetabular cup 10 into the acetabulum will now be described with reference to FIGS. 11 and 12.

The acetabulum is prepared in the conventional manner by reaming the acetabulum until a pre-operatively selected size is achieved. Any osteophytes are removed and soft tissue cleared from the acetabular margin. If required, a bore is made in the acetabulum for receiving the supero medial peg 26.

The appropriate sized acetabular cup 10 is mounted to the head 84 of the introducing tool 80 in the manner previously described such that flange 98 overlies flange 30 and so that guide apertures 99 are aligned with apertures 36. The introducing tool 80 is then used to position the acetabular cup 10 within the acetabulum such that the flange 30 lies on the superior side. However, it will be understood that the acetabular cup 10 may be orientated differently if adequate fixation may be achieved with the flange 30 in a different location. The acetabular cup 10 is then firmly impacted into position.

When the acetabular cup orientation is set and stable a small drill guide tube, not shown, is introduced into one of the guide apertures 99. The small drill guide tube projects upwardly from flange 98 and away from the acetabular cup 10 and serves to guide a drill bit for drilling a pilot hole 113 in the bone underlying flange 30. Because the second portion 34 of the flange 30 is inclined with respect to the first portion 32 it is able to overly more closely the bone surrounding the acetabulum with the result that the small drill guide tube (and indeed the tap guide tube referred to subsequently) extends substantially perpendicularly to the bone underlying the flange 30. This in turn means that the pilot hole 113 may also be formed substantially perpendicularly to the surface of the bone underlying the flange 30 leading to enhanced fixation of the acetabular cup 10. If desired the guide aperture 99 may be internally threaded to threadingly engage an external thread provided on one end of the small drill guide tube. Once the pilot hole 113 has been drilled, the small drill guide tube is then removed from the guide aperture 99 and a depth gauge, not shown, is used to assess the correct length of the fixation member 50 to be used.

Figure 11:
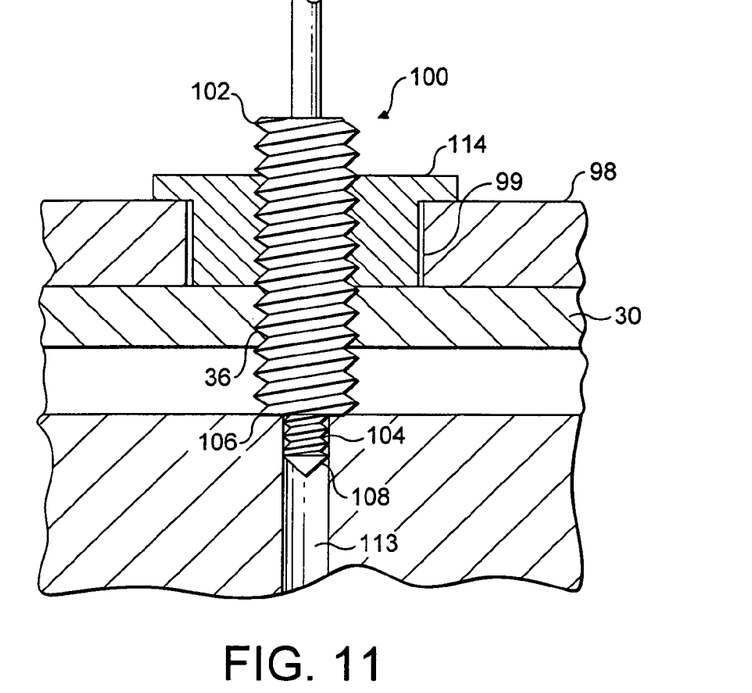
FIG. 11 shows a detailed cross-sectional view of the tap of FIG. 10 when in use.
Figure 12:
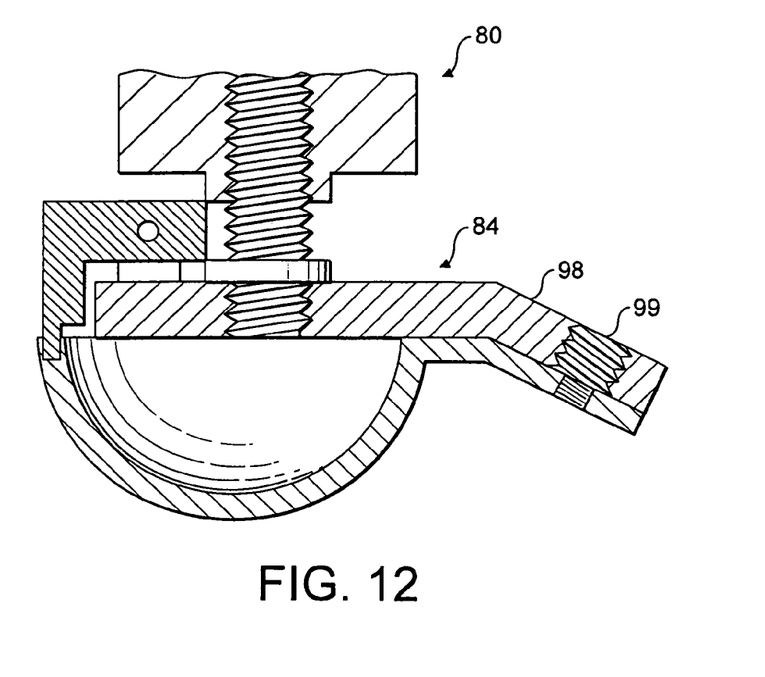
FIG. 12 shows a cross-sectional view of the acetabular cup of FIG. 1 in combination with the introducing tool of FIG. 8.

A tap guide tube 114 similar to the small drill guide tube is then introduced into the guide aperture 99 as shown in FIG. 11. The starter tap 100 is introduced into the tap guide tube 114 such that the tip 108 passes first through the guide aperture 99 and then through aperture 36. As the starter tap 100 is advanced so it is rotated such that the external helical thread 110 on the upper portion 102 engages with the internal thread 38 of the aperture 36. Because the length $L_1$ of the upper portion 102 is significantly longer than the length $L_2$ of the lower portion 106 it can be ensured that this threaded engagement occurs before tip 108 of the starter tap 100 engages the bone. Nonetheless, further rotation of the starter tap 100 causes the tip 108 to be introduced into the previously drilled pilot hole 113. As the starter tap 100 continues to rotate, the cutting edge 112 provided on the exterior of the lower portion 104 cuts the start of a thread configuration on an interior surface of the previously drilled pilot hole 113. However, since the external helical thread 110 on the upper portion 102 engages with the internal thread of the aperture 36 before the cutting edge 112 engages with the pilot hole 113, it is possible to ensure that the thread configuration that is cut in the pilot hole 113 forms a continuation of the same helix defined by the internal thread of the aperture 36 albeit of reduced radius.

Because the starter tap 100 is intended to only cut the first few rotations of a thread configuration within the pilot hole 113, the length $L_2$ of the lower portion is made deliberately short. As a result continued rotation of the starter tap 100 soon brings the radially projecting shoulder 106 into engagement with the bone surrounding the pilot hole 113. The surgeon will feel this and cease further rotation of the starter tap 100. The starter tap 100 is then rotated in the opposite direction to remove the starter tap from the tap guide tube 114.

A second, full length tap, not shown, may then be introduced through the tap guide tube 114 and aperture 36 to fully tap the pilot hole 113. The use of the tap guide tube 114 provides enhanced accuracy and ensures that the hole is tapped centrally.

The above procedure is then repeated for as many of the remaining guide apertures 99 as required.

Following preparation of the fixation holes a fixation member 50 is offered up to one of the guide apertures 99 with the introducing tool 80 still in position. The tip 70 of the fixation member 50 passes through the guide aperture 99 and the threaded aperture 36 and into the now fully tapped pilot hole 113. Rotation of the fixation member 50 by means of the hexagonal drive causes the thread configuration on the lower portion 56 to threadingly engage with the newly cut thread configuration on the interior surface of the pilot hole 113 before the thread configuration on the upper portion 52 threadingly engages the threaded aperture 36. Nonetheless, continued rotation of the fixation member 50 does eventually bring the thread configuration on the upper portion 52 into threaded engagement with the threaded aperture 36. However, because the thread configuration on the lower portion 56 is a continuation of the helix defined by the thread configuration on the upper portion 52 and because the newly cut thread configuration in the pilot hole 113 is a continuation of the helix defined by the thread of the threaded aperture 36, the simultaneous engagement of both pairs of threads does not produce a reaction force similar to that experienced in prior art arrangements which tend to push the acetabular cup 10 out of engagement with the acetabulum.

As the fixation member 50 continues to be rotated, the frustroconical head 60 passes through the guide aperture 99 and into engagement with a correspondingly shaped bevel surrounding the threaded aperture 36. When the fixation member 50 has been fully screwed home the head 60 lies flush with an upper surface of the flange 30. Nonetheless, the act of maintaining the introducing tool 80 in position whilst the fixation member 50 is introduced provides stability against rotational movement of the acetabular cup 10 as the fixation member 50 is tightened.

The process is repeated for a second and subsequent fixation members 50 as required and the stability of the acetabular cup 10 in the acetabulum is then assessed.

Although the above apparatus and method is described for use in the insertion of an acetabular cup the invention is not so limited. It will be apparent that a cup corresponding to other ball and socket joints in the body, for example the shoulder joint, may also benefit from the enhanced fixation of the cup (in the socket) provided by the present invention.

The fixation member, and method preparation of the pilot hole for receiving such a fixation member, may also find use in the fixation of other implants in the body, where it is desired, for example, to alleviate the problems caused by the reaction forces generated when inserting screws into bone, or other material. In this regard it will be noted that, as with the small drill guide tube, the tap guide tube 114 may be externally threaded at one end to threadingly engage an internal thread provided in the guide aperture 99. Likewise, although the starter tap 100 has been described as comprising an upper portion 102 and a lower portion 104 that meet at a radially projecting shoulder 106, this need not necessarily be the case. The two portions 102 and 104 could merge via a tapered intermediate portion and the surgeon would still feel sufficient resistance when in use for him to know when the first few rotations had been cut in the pilot hole and when to cease further rotation.

What is claimed is:

1. A bone tapping kit for cutting an internal thread in bone defining a bore, the kit comprising:
    a guide component adapted to overlie the bone and having a threaded aperture in alignment with the bore; and
    a tap comprising a first portion having a first diameter and a second portion having a second diameter, the second diameter being smaller than the first diameter, the first portion having an external thread adapted to threadingly engage the threaded aperture of the guide component and the second portion having a helical cutting edge adapted to be received within the bore and cut the internal thread, the guide component and the tap being relatively dimensioned such that upon introduction of the tap into the threaded aperture with the second portion towards the bone, the first portion of the tap threadingly engages the threaded aperture before the helical cutting edge engages the bone when the guide component overlies the bone and the tap is rotated relative to the guide component.

2. The kit as claimed in claim 1, wherein the second portion of the tap comprises an axial length, and the threaded aperture defines an axis and comprises an axial dimension which is greater than the axial length of the second portion of the tap.

3. The kit as claimed in claim 1, wherein the tap further comprises a shoulder, and the first portion and second portion are contiguous and meet at the shoulder.

4. The kit as claimed in claim 1, wherein the tap further comprises an intermediate portion, and the first and second portions are interconnected by said intermediate portion, the intermediate portion tapering from the first diameter adjacent the first portion to the second diameter adjacent the second portion.

5. The kit as claimed in claim 1, wherein the external thread of the first portion defines a helix, the helical cutting edge provided on the second portion of the tap having the same pitch as the external thread provided on the first portion of the tap and the same angular displacement as a continuation of the helix defined by said external thread.

6. The kit as claimed in claim 1, wherein the helical cutting edge provided on the second portion of the tap is adapted to cut an internal thread capable of threaded engagement with a corti/cancellous bone thread.

7. The kit as claimed in claim 1, wherein the guide component comprises a prosthetic device to be secured to the bone by means of a fixation member passing through the threaded aperture.

8. The kit as claimed in claim 7, wherein the prosthetic device comprises a cup for use in a ball and socket joint, the cup comprising an outer surface, an inner articulating surface, and a flange extending outwardly from the cup and away from the inner articulating surface, the threaded aperture being provided in said flange.

9. The kit as claimed in claim 7, wherein the prosthetic device comprises a prosthetic cup for use in a ball and socket joint, the cup comprising an outer surface, an inner articulating surface, a rim extending between the outer surface and the inner articulating surface and a flange extending outwardly from the cup and away from the inner articulating surface, at least a portion of the flange being inclined with respect to a plane defined by the rim and having an aperture adapted to receive a fixation member.

10. The kit as claimed in claim 7 further comprising a bone/prosthesis fixation member comprising a first fixation member portion having a first fixation member diameter and a first fixation member thread configuration and a second fixation member portion having a second fixation member diameter and a second fixation member thread configuration, the second fixation member diameter being smaller than the first fixation member diameter and the second fixation member thread configuration having the same pitch as the first fixation member thread configuration and the same angular displacement as a continuation of the helix defined by the first fixation member thread configuration.

11. The kit as claimed in claim 10, wherein the first fixation member thread configuration and the external thread provided on the first portion of the tap are both adapted to threadingly engage the threaded aperture of the guide component.

12. The kit as claimed in claim 10, wherein the second fixation member thread configuration is adapted to threadingly engage the internal thread cut by the helical cutting edge provided on the second portion of the tap.

13. The kit as claimed in claim 12, wherein, upon removal of the tap from the guide component and introduction of the fixation member into the threaded aperture, the second fixation member thread configuration threadingly engages the internal thread cut by the helical cutting edge provided on the second portion of the tap before the first fixation member thread configuration threadingly engages the threaded aperture of the guide component.

14. A method of cutting an internal thread in a bone defining a bore, the method comprising the steps of:
    providing a guide component having a threaded aperture;
    aligning the threaded aperture with the bore;
    providing a tap comprising a first portion having a first diameter and a second portion having a second diameter, the second diameter being smaller than the first diameter, the first portion having an external thread defining a helix and adapted to threadingly engage the threaded aperture of the guide component and the second portion having a helical cutting edge adapted to be received within the bore, the helical cutting edge having the same pitch as the external thread provided on the first portion and the same angular displacement as a continuation of the helix defined by the external thread;
    introducing the tap into the threaded aperture of the guide component with the second portion directed towards the bone;
    threadingly engaging the first portion of the tap with the threaded aperture before engaging the helical cutting edge with the bone; and
    rotating the tap relative to the guide component to engage the bore while maintaining said threaded engagement between the tap and the threaded aperture.

15. A method of securing a prosthesis with respect to a bone defining a bore, the method comprising the steps of:
    providing the prosthesis defining a threaded aperture;
    providing a fixation member comprising a first portion having a first diameter and a first thread configuration and a second portion having a second diameter and a second thread configuration, the second diameter being smaller than the first diameter, the first thread configuration being adapted to threadingly engage the threaded aperture of the prosthesis and the second thread configuration having the same pitch as the first thread configuration and the same angular displacement as a continuation of the helix defined by the first thread configuration;

aligning the threaded aperture with the bore;

providing a tap comprising a first portion having a first diameter and a second portion having a second diameter, the second diameter being smaller than the first diameter, the first portion having an external thread defining a helix and adapted to threadingly engage the threaded aperture of the prosthesis and the second portion having a helical cutting edge adapted to be received within the bore, the helical cutting edge having the same pitch as the external thread provided on the first portion and the same angular displacement as a continuation of the helix defined by the external thread;

introducing the tap into the threaded aperture of the prosthesis with the second portion directed towards the bone;

threadingly engaging the first portion of the tap with the threaded aperture before engaging the helical cutting edge with the bone; and rotating the tap relative to the prosthesis to cut an internal thread in the bore;

removing the tap;

introducing the fixation member through the threaded aperture with the second portion directed towards the bone; and threadingly engaging the second thread configuration with the internal thread before engaging the first thread configuration with the threaded aperture.

* * * * *